United States Patent [19]
Cockrill

[11] Patent Number: 5,263,941
[45] Date of Patent: Nov. 23, 1993

[54] NEONATAL VENTILATOR CIRCUIT HOLDER

[76] Inventor: Janice M. Cockrill, 4 Farmington Ct., Little Rock, Ark. 72207

[21] Appl. No.: 945,389

[22] Filed: Sep. 16, 1992

[51] Int. Cl.$^5$ .......................................... A61M 25/02
[52] U.S. Cl. .............................. 604/179; 128/DIG. 6; 128/DIG. 26
[58] Field of Search ................. 604/174, 179, 180; 128/DIG. 26, DIG. 6

[56] References Cited

U.S. PATENT DOCUMENTS

| | | | |
|---|---|---|---|
| 1,567,225 | 12/1925 | Barbin . | |
| 2,199,869 | 5/1940 | Baker et al. | 248/102 |
| 3,726,280 | 4/1973 | Lacount | 604/179 |
| 4,018,221 | 4/1977 | Rennie | 128/DIG. 26 |
| 4,096,863 | 6/1978 | Kaplan et al. | 128/349 |
| 4,309,642 | 1/1982 | Hexman | 128/DIG. 26 |
| 4,333,468 | 6/1982 | Geist | 128/DIG. 26 |
| 4,416,664 | 11/1983 | Womack | 604/179 |
| 4,548,200 | 10/1985 | Wapner | 604/179 |
| 4,574,798 | 3/1986 | Heitzman | 128/205.22 |
| 4,591,356 | 5/1986 | Christie | 604/179 |
| 4,671,787 | 6/1987 | Widman | 604/179 |
| 4,702,736 | 10/1987 | Kalt et al. | 128/DIG. 26 |
| 4,739,757 | 4/1988 | Edwards | 128/DIG. 26 |
| 4,759,963 | 7/1988 | Uso, Jr. et al. | 428/100 |
| 4,774,946 | 10/1988 | Ackerman et al. | 128/DIG. 26 |
| 4,799,923 | 1/1989 | Campbell | 604/179 |
| 4,838,873 | 6/1989 | Kalt et al. | 128/DIG. 26 |
| 4,988,338 | 1/1991 | Taylor et al. | 128/DIG. 26 |

*Primary Examiner*—Paul J. Hirsch
*Attorney, Agent, or Firm*—Jacobson, Price, Holman & Stern

[57] ABSTRACT

A neonatal ventilator circuit holder including a strap for securely holding a ventilator circuit in place on a mattress adjacent to an infant in order to retain the ventilator circuit in optimum relation to the mouth of an infant reclining on the mattress. The holder is in the form of an elongated strap of flexible fabric or similar material having the ends thereof secured to the frame of the infant bed by the use of readily attachable and detachable fastening structures preferably in the form of hook and loop pile fasteners available under the trademark "VELCRO". Attached to the upper surface of the strap is a pair of shorter and relatively narrow retaining straps or flaps oriented in longitudinally spaced relation and secured to the mattress engaging strap by continuous areas of hook and loop pile fasteners with either of the shorter and narrower straps overlying and retaining a ventilator circuit in generally adjacent and parallel relation to the upper surface of the mattress in order to securely hold the ventilator circuit to the bed and prevent the ventilator circuit from sliding off the mattress and disconnecting the endotracheal tube from the infant.

10 Claims, 1 Drawing Sheet

NEONATAL VENTILATOR CIRCUIT HOLDER

BACKGROUND OF THE INVENTION

1. Field of the Invention

The present invention generally relates to a neonatal ventilator circuit holder and more specifically to a strap for securely holding a ventilator circuit in place on a mattress adjacent to an infant in order to retain the ventilator circuit in optimum relation to the mouth of an infant reclining on the mattress. The holder is in the form of an elongated strap of flexible fabric or similar material having the ends thereof secured to the frame of the infant bed by the use of readily attachable and detachable fastening structures preferably in the form of hook and loop pile fasteners available under the trademark "VELCRO". Attached to the upper surface of the strap is a pair of shorter and relatively narrow retaining straps or flaps oriented in longitudinally spaced relation and secured to the mattress engaging strap by continuous areas of hook and loop pile fasteners with either of the shorter and narrower straps overlying and retaining a ventilator circuit in generally adjacent and parallel relation to the upper surface of the mattress in order to securely hold the ventilator circuit to the bed and prevent the ventilator circuit from sliding off the mattress and disconnecting the endotracheal tube from the infant.

2. Description of the Prior Art

Various devices have been provided to retain objects in relation to components of a bed, crib and the like and an infant positioned in the bed or crib. Such devices include structures for supporting baby bottles in position for access. Also, devices are known for holding catheters or IV tubes in relation to a portion of the human anatomy. The following U.S. Pat. Nos. relate to this field of endeavor.

1,567,225
2,199,869
4,096,863
4,574,798
4,671,787
4,759,963

None of the prior art discloses an elongated strap anchored to the bed or bed frame combined with narrow flaps or straps on its upper surface to securely retain a neonatal ventilator circuit in place adjacent to the infant by using hook and loop pile fastener material on the strap attached to the bed or bed frame and the narrow straps or flaps on its upper surface.

SUMMARY OF THE INVENTION

An object of the present invention is to provide a holder for a neonatal ventilator circuit for retaining the ventilator circuit and endotracheal tube securely in adjacent and generally aligned relation to the mouth of a neonate or infant reclining on the surface of a mattress supported by a bed or crib frame.

Another object of the invention is to provide a neonatal ventilator circuit holder in the form of an elongated flexible strap which extends transversely across the upper surface of a mattress adjacent one end thereof with the ends of the strap being securely anchored to the bed, bed frame, crib or crib frame by the use of readily separable fasteners structures such as patches of hook and loop pile fasteners available under the trademark "VELCRO" to enable easy assembly and disassembly of the holder.

A further object of the invention is to provide a neonatal ventilator circuit holder as set forth in the preceding objects in which the mattress strap is provided with a pair of shorter and narrower retaining flaps or straps on the upper surface thereof which are oriented in longitudinally spaced relation and extending inwardly from the outer ends and along the center line of the mattress strap with the upper surface of the mattress strap and the downwardly facing surface of each of the narrow flaps being provided with continuous areas of hook and loop pile fasteners which enables a ventilator circuit to be positioned against the upper surface of the mattress strap in generally perpendicularly relation thereto with the flap then being positioned across the upper surface of the rigid ventilator circuit and secured in place by the hook and loop pile fasteners thereby retaining the neonatal ventilator circuit securely across the top surface of the mattress strap and in adjacent, generally parallel relation to the upper surface of the mattress and generally in alignment with the mouth of an infant reclining on the mattress thereby securely holding the ventilator circuit in optimum relation to the infant using the ventilator circuit.

Still another object of the invention is to provide a neonatal ventilator circuit holder which is easy to use, effective in securely holding a ventilator circuit in optimum relation to an infant and is simple and long lasting in construction.

These together with other objects and advantages which will become subsequently apparent reside in the details of construction and operation as more fully hereinafter described and claimed, reference being had to the accompanying drawings forming a part hereof, wherein like numerals refer to like parts through-out.

DESCRIPTION OF THE PREFERRED EMBODIMENT

Figure 1:
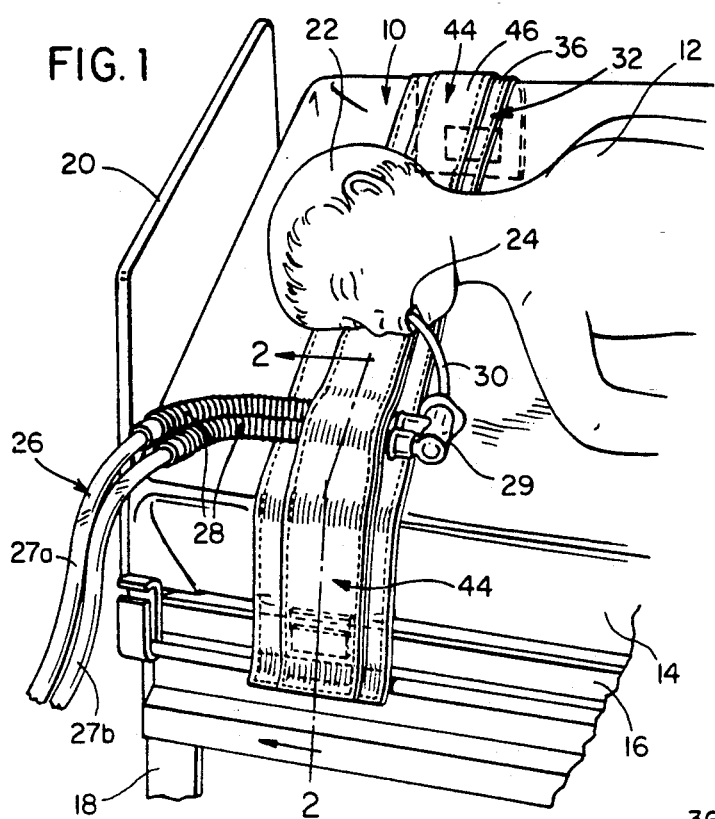
FIG. 1 is a perspective view of the neonatal ventilator circuit holder of the present invention illustrating the manner in which the holder retains a ventilator circuit in optimum relation to the mouth of an infant positioned on the mattress.
Figure 6:
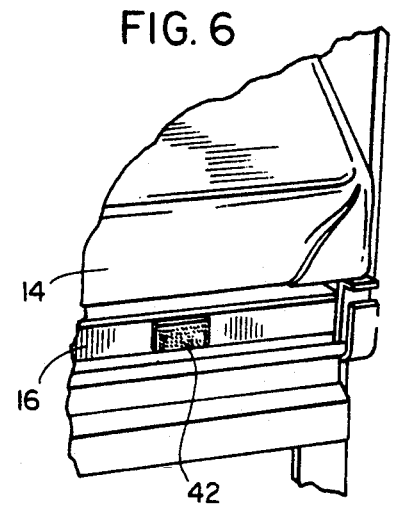
FIG. 6 is a fragmental perspective view of the bed or crib frame illustrating a patch of hook and loop pile fastener secured to the bed frame.
Figure 4:
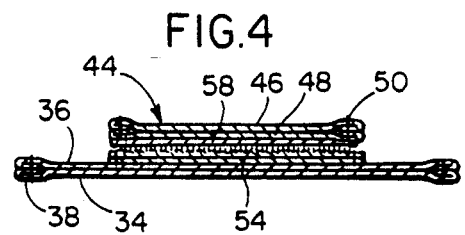
FIG. 4 is a transverse sectional view along section line 4—4 on FIG. 3 illustrating the manner in which the hook and loop pile fasteners secure the retaining straps or flaps to the mattress strap.

Referring now specifically to the drawings, the neonatal ventilator circuit holder of the present invention is generally designated by reference numeral 10 and is associated with a bed, crib or other structure on which a neonate or infant 12 can recline and includes a mattress 14, a supporting frame 16, legs 18 and a headboard 20. It is pointed out that the structure of the bed and mattress may vary since neonates frequently are supported in an open topped, transparent carrier to facilitate handling and treatment when in a nursery in a hospital or the like. Also, the neonate 12 is represented schematically in which the head 22 is positioned with the mouth 24 oriented laterally and generally horizontally toward either side of the mattress 14. The holder 10 functions to securely hold a neonatal ventilator circuit 26 in optimum relation to the infant 12. The ventilator circuit 26 includes an exhalation tube 27a and an inhalation tube 27b which are connected together with a Y-connector 29 and an endotracheal tube 30 extends into the mouth 24 of the infant 12 in a known manner. A generally rigid portion 28 of the two tubes of the neonatal ventilator circuit are held adjacent and generally parallel to the upper surface of the mattress 14 and the endotracheal tube 30 is oriented for positioning in the mouth 24 of the infant 12 as illustrated in FIG. 1 in order for the ventilator circuit 26 to function properly to maintain the infant properly ventilated.

The holder 10 includes an elongated flexible strap 32 of fabric material preferably constructed of two layers 34 and 36 of fabric which are hemmed and stitched along the edges thereof as at 38. The bottom surface of the strap 32 is provided with a patch of hook and loop pile fastener material 40 adjacent each end thereof which is stitched to the layers 34 and 36 of the strap 32. The bed frame 16 is provided with a patch of hook and loop pile fastener material 42 at each side of the bed which can be adhesively attached to the frame to cooperate with the fastener material 40 on the strap 32 to securely anchor the strap 32 in transversely extending relation across the upper surface of the mattress 14 and downwardly along the outer side surfaces of the mattress 14 and connected to the bed frame 16 as specifically illustrated in FIG. 2.

Figure 2:
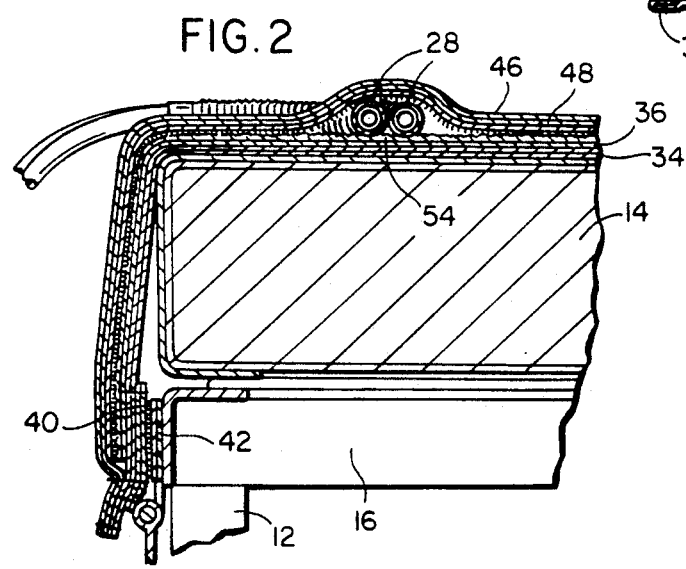
FIG. 2 is a sectional view, on an enlarged scale, taken along section line 2—2 on FIG. 1 illustrating the specific structure of the holder of the present invention including the association of the ventilator circuit with the holder.
Figure 5:
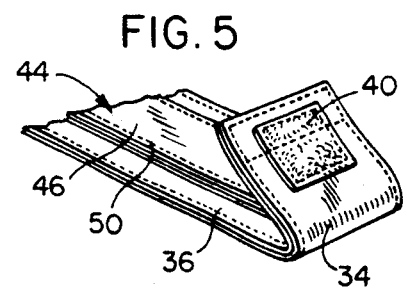
FIG. 5 is a fragmental perspective view illustrating the end of the mattress strap turned upwardly and inwardly to illustrate the patch of hook and loop pile fastener on the lower surface thereof.
Figure 3:
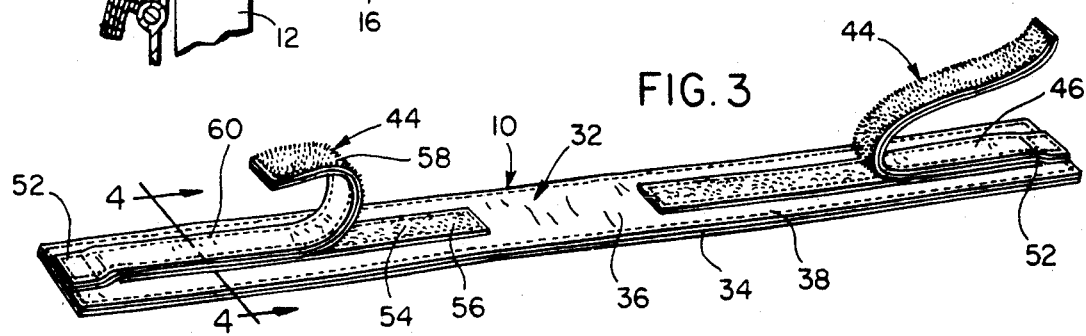
FIG. 3 is a perspective view of the holder with the retaining straps or flaps on the upper surface thereof being shown in a partial open position.

Attached to the upper surface of the mattress strap 32 is a pair of short, narrow retaining straps or flaps 44 which extend inwardly from the outer ends of the strap 32 and are oriented in longitudinally spaced relation. Each of the retaining straps or flaps 44 includes an outer layer 46 and an inner layer 48 of fabric material having the side edges hemmed and stitched at 5 with the outer ends being stitched to the strap 32 at 52. Attached to the upper surface of the strap 32 is an elongated patch of hook and loop pile fastener material 54 secured thereto by stitching 56 The bottom surface of each of the retaining straps or flaps 44 is also provided with a continuous patch of hook and loop pile fastener material 58 secured thereto by the stitching 50. The retaining straps or flaps 44 completely cover the hook and loop pile fastener material 54 and will be positioned against the upper surface of the strap 32 when in the closed position. Each of the retaining straps or flaps can be moved toward an open position by grasping the inner free end thereof and pulling it upwardly as illustrated in FIG. 3 to enable the ventilator circuit 26 to be positioned transversely across the strap 32 after which the retaining strap or flap 44 is lowered and secured in place by the hook and loop pile fastener material to securely hold the ventilator circuit 26 adjacent the upper surface of the mattress 14 and in a position that will provide optimum relation between the endotracheal tube 30 and the mouth 24 of the infant 12 as illustrated in FIGS. 2 and 3.

While dimensions of the holder may vary, it has been found in actual practice that the strap 32 may be constructed of two pieces of fabric approximately 26½ inches in length and 4 inches in width sewed together to provide durability and strength. The two squares of the loop component of the hook and loop fastener attached to the bottom surface at the outer end of the strap 32 may be approximately two inches square and are used to secure the holder to the infant bed by the use of two self adhesive pieces 42 which are approximately two inches in length and one inch in width and include the hook component of the hook and loop fastener material. The strap 32 is then laid across the bed with one end of the strap being affixed to the side of the bed frame by the fastener material and the strap is then pulled tight across the mattress and the other end affixed to the corresponding patch 42 on the bed frame thus securely holding the strap in place. The retaining straps or flaps 44 are also of two pieces of fabric material approximately 10½ inches in length and 2½ inches in width with the outer end sewed to the strap 32 and including the hook component 58 of the hook and loop pile fastener material on the under surface thereof with the corresponding loop component of the hook and loop pile fastener material being secured to the upper surface of the strap 32 thus assuring that if any portion of the loop component of the fastener material 54 is exposed, it will not irritate the head or other surface area of the infant. With the strap 32 secured in place, either of the retaining straps or flaps 44 can be opened and a ventilator circuit 26 placed across the strap 32 and the retaining strap 44 then closed over the ventilator circuit as illustrated in FIGS. 1 and 2. This securely holds the ventilator circuit to the bed and prevents the circuit from sliding off the mattress and disconnecting the endotrachal tube 30 from the infant. This structure provides secure retention of the neonatal ventilation circuit in optimum relation to the infant and the use of "VELCRO" enables the holder to be quickly and easily assembled when necessary to use and easily removed when desired.

The foregoing is considered as illustrative only of the principles of the invention. Further, since numerous modifications and changes will readily occure to those skilled in the art, it is not desired to limit the invention to the exact construction and operation shown and described, and, accordingly, all suitable modifications and equivalents may be resorted to, falling within the scope of the invention.

What is claimed as new is as follows:

1. A holder for a neonatal ventilation circuit comprising an elongated strap, said strap being positioned transversely of the upper surface of a mattress supported on a bed frame and in underlying relation to the head of an infant reclining on the mattress, means on each end of the strap anchoring it to the bed frame, a retaining flap positioned in overlying relation to a portion of the strap extending across the mattress, one end of the retaining flap being secured to the strap extending across the mattress adjacent an outer end thereof and the other end of the retaining flap being free, fastener means throughout the length of the retaining flap for securing the retainer flap to the strap which extends across the mattress to enable a neonatal ventilation circuit to be positioned transversely across the strap extending across the mattress and retained in that position by said retaining flap overlying the neonatal ventilation circuit thereby retaining the neonatal ventilation circuit adjacent the surface of the mattress and in optimum relation to the mouth of an infant reclining on the mattress without attachment to the infant.

2. The holder as defined in claim 1 wherein said means securing the retaining flap throughout its length to the strap extending across the mattress includes continuous hook and loop pile fastener material secured to the under surface of the retaining flap and to the upper surface of the strap extending across the mattress to enable the retaining flap to snugly and securely engage the neonatal ventilation circuit extending across the strap which engages the mattress.

3. The holder as defined in claim 2 wherein said means anchoring the strap across the mattress includes hook and loop pile fastener means on the ends of the strap and on portions of a bed frame.

4. The holder as defined in claim 1 wherein said strap extending across the mattress includes a retaining flap at both ends thereof which are oriented in spaced relation to each other to enable a neonatal ventilator circuit to be securely held on either side of an infant reclining on the mattress.

5. The holder as defined in claim 4 wherein said strap and flaps are constructed of flexible fabric material with the strap being longer and wider than either of the retaining flaps.

6. The combination of a neonatal ventilator circuit including an endotracheal tube and a holder for securely retaining the circuit in optimum relation to an infant reclining on a mattress, said holder comprising an elongated strap extending fixedly across the upper surface of the mattress in underlying relation to the head of an infant reclining on the mattress, and retaining means on said strap for releasably securing said neonatal ventilator circuit to the strap and in adjacent relation to the surface of the mattress and retaining the endotracheal tube in optimum relation to the mouth of the infant.

7. In combination with a bedding assembly including a mattress for supporting a neonate in reclining position, a neonatal ventilation circuit holder mounted on said bedding assembly retaining the neonatal ventilation circuit in optimal relation to the mouth of the neonate on the mattress, said holder comprising an elongated, flexible strap extending completely across an upper surface of said mattress in underlying relation to the head of the neonate on the mattress, means located only at outer end portions of the strap to anchor the strap to the bedding assembly in remote relation to the head of the neonate on the mattress thereby anchoring the strap to the bedding assembly solely by the attachment means at the outer ends of the strap, a retaining flap of flexible material having a length substantially less than the length of said strap, said flap including an outer end portion permanently secured to an upper surface of said strap adjacent an outer end of the strap, the bottom surface of the flap and the upper surface of the strap including coacting means enabling the portion of the flap inwardly of the outer end portion to be releasably attached to the upper surface of said strap, said neonatal ventilation circuit including tube means extending transversely of the strap for positioning a ventilation tube in optimum relation to the mouth of a neonate reclining on the mattress with the head of the neonate positioned on said strap, said tube means extending transversely of the strap in underlying relation to the retaining flap with the flap retaining the tube means in anchored relation to the strap and bed assembly.

8. The combination as defined in claim 7 wherein said bed assembly includes a frame structure, said attaching means at each end of the strap including means detachably engaging the frame structure below the upper surface of the mattress.

9. The combination as defined in claim 7 wherein said strap is provided with a width engaging a major length portion of the head of a neonate.

10. The combination as defined in claim 7 wherein said retaining flap extends longitudinally of the strap a distance less than one half the total length of the strap and a second retaining flap at the other end of said strap with both of said retaining flaps being identical in construction to enable the neonatal ventilation circuit to be oriented to either side of the head of a neonate reclining on the mattress.

* * * * *